US006190673B1

(12) United States Patent
Guskey et al.

(10) Patent No.: US 6,190,673 B1
(45) Date of Patent: *Feb. 20, 2001

(54) GEL COMPOSITIONS CONTAINING GELLANTS IN THE FORM OF ALKYL AMIDES OF TRI-CARBOXYLIC ACIDS

(75) Inventors: Gerald John Guskey, Montgomery; David Frederick Swaile, Cincinnati, both of OH (US)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/771,090

(22) Filed: Dec. 20, 1996

(51) Int. Cl.⁷ ............................... A61K 7/02; A61K 9/00
(52) U.S. Cl. .................... 424/401; 514/613; 514/944; 424/68; 252/315.1; 516/DIG. 7; 564/192; 564/193
(58) Field of Search .................... 514/613, 944; 564/192, 193; 424/65; 516/DIG. 7

(56) References Cited

U.S. PATENT DOCUMENTS

| | | | |
|---|---|---|---|
| 2,328,021 | * 8/1943 | Katzman et al. | 564/193 |
| 2,890,987 | 6/1959 | Hilfer | 167/90 |
| 2,900,306 | 8/1959 | Slater | 167/90 |
| 3,255,082 | 6/1966 | Barton | 167/90 |
| 3,792,068 | 2/1974 | Luedders | 260/429.3 |

(List continued on next page.)

FOREIGN PATENT DOCUMENTS

| | | | |
|---|---|---|---|
| 1266003 | 4/1986 | (CA) | A61K/7/32 |
| 2054478 | 5/1992 | (CA) | A61K/7/32 |
| 2531469 | * 1/1977 | (DE) | 564/193 |
| 0 295 070 | 12/1988 | (EP) | A61K/7/32 |
| 0 295 071 | 12/1988 | (EP) | A61K/7/32 |
| 0 396 137 | 11/1990 | (EP) | A61K/7/32 |
| 0 448 278 | 9/1991 | (EP) | A61K/7/38 |
| 530 866 | 3/1993 | (EP) | C07C/305/06 |
| 530866 A1 | 3/1993 | (EP) | A61K/7/48 |
| 0 616 842 A1 | 9/1994 | (EP) | B01J/13/00 |
| 0 682 940 A1 | 11/1995 | (EP) | A61K/7/48 |
| 1485694 | 9/1977 | (GB) | B01F/17/28 |
| 2253347 | 9/1992 | (GB) | A61K/7/32 |
| 2299024 | 9/1996 | (GB) | A61K/7/32 |
| 61-206 450 | 9/1986 | (JP) | A61L/9/01 |
| 62-265393 | 11/1987 | (JP) | C10L/3/00 |
| 10-20286 | 1/1989 | (JP) | C09K/3/00 |
| 64-62377 | 3/1989 | (JP) . | |
| 1-207223 | 8/1989 | (JP) | A61K/7/02 |
| 2-180805 | 7/1990 | (JP) | A61K/7/00 |
| 2-264707 | 10/1990 | (JP) . | |
| 3-170415 | 7/1991 | (JP) | A61K/7/32 |
| 42 08 202 | 7/1992 | (JP) | A01N/25/18 |
| WO 96/26709 | 9/1996 | (WO) | A61K/7/32 |

OTHER PUBLICATIONS

M. F. Bobin, C. Suzza and M–C. Martini, "Using Fluorinated Compounds in Topical Preparations", 111*Cosmetics and Toiletries* 47–63, Oct., 1996.

Taro Tachibana and Hideko Kambara, "Studies of Helical Aggregates on Molecules. I. Enantiomorphism in the Helical Aggregates of Optically Active 12–Hydroxystearic Acid and Its Lithium Salt", *Bulletin of the Chemical Society of Japan*, vol. 42, 3422–3424 (1969).

Taro Tachibana, Shyoko Kitazawa and Hideko Takeno, "Studies oh Helical Aggregates of Molecules. II,The Sense of Twist in the Fibrous Aggregates from the Alkali Metal Soaps of Optically Active 12–Hydroxystearic Acid ", Bulletin of Chemical Society of Japan, vol. 43 2418–2421 (1970).

"Electron Microscopic and Thermal Studies of Optically Active 12–Hydroxystearic Acids in Soap Formation", Journal of Colloid and interface Science, vol. 51, No. 2, May 1975.

"Morphology of Collapsed Monolayers of Optically Active and Racemic 12–Hydroxystearic Acids", *Journal of Colloid and Interface Science*, vol. 61, No. 2, Sep. 1977.

C. D. Vaugh, "Solubility Effects in Product, Package, Penetration and Preservation" 103 *Cosmetics and Toiletries* 47–69, Oct., 1988.

Plechner, *Antiperspirants and Deodorants*, 2 Cosmetics, Science and Technology, Balsam and Sagarin, 374–400, 1972.

Homma, Masao, Oil Gelating Agent Utilizing Amino Acids, (Modern Chemistry), 54–59, Aug., 1987 (Translation).

C. D. Vaughn, "Using Solubility Parameters in Cosmetics Formulation", 36 *J. Soc. Cosmetic Chemists* 319–333 Sep./Oct., 1985.

Tsau, Heller and Pratap, "Thermoreversible Organogels of 12–Hydroxystearic Acid", *Polymer Preprints* 1994 35, 737–738.

Balsam and Sagarin, Cosmetics, Science, and Technology, vol. 1, 27–104, 1972.

Geria, "Formulation of Stick Antiperspirants and Deodorants", *Cosmetics and Toiletries*, 99:55–60 (1984).

Gels and Sticks Formulary, 99 *Cosmetics and Toiletries* 82–87, 1984.

Todd et al., "Volatile Silicone Fluids for Cosmetics", *Cosmetics and Toiletries*, 91:29–32 (1976).

Chemical Abstracts, vol. 85, No. 2, Jul. 12, 1976 No. 85:10310.

Taro Tachibana, Tomoko Mori and Kayako Hori, "New type of twisted mesophase in jellies and solid films of chiral 12–hydroxyoctadecanoic acid", *Nature*, vol. 278, Apr. 1979.

(List continued on next page.)

*Primary Examiner*—Peter F. Kulkosky
(74) *Attorney, Agent, or Firm*—William J. Winter; Lucy Elandjian; Darryl C. Little

(57) ABSTRACT

The present invention relates to gel compositions comprising alkyl amides of tri-basic carboxylic acids and methods of making gel compositions.

18 Claims, No Drawings

U.S. PATENT DOCUMENTS

| | | | |
|---|---|---|---|
| 3,887,692 | 6/1975 | Gilman | 423/462 |
| 3,903,258 | 9/1975 | Siegal | 424/66 |
| 3,904,741 | 9/1975 | Jones et al. | 423/462 |
| 3,969,087 | 7/1976 | Saito et al. | 44/7 C |
| 3,970,748 | 7/1976 | Mecca | 424/68 |
| 3,979,510 | 9/1976 | Rubino | 424/47 |
| 3,981,896 | 9/1976 | Pauling | 260/429 |
| 4,017,599 | 4/1977 | Rubino | 424/47 |
| 4,049,792 | 9/1977 | Elsnau | 424/66 |
| 4,053,581 | 10/1977 | Pader et al. | 424/68 |
| 4,126,679 | 11/1978 | Davy et al. | 424/66 |
| 4,137,306 | 1/1979 | Rubino | 424/68 |
| 4,147,766 | 4/1979 | Kozischek | 424/14 |
| 4,151,272 | 4/1979 | Geary | 424/68 |
| 4,154,816 | 5/1979 | Roehl et al. | 424/68 |
| 4,202,879 | 5/1980 | Shelton | 424/66 |
| 4,226,889 | 10/1980 | Yuhas | 424/59 |
| 4,371,645 | 2/1983 | Mahaffey, Jr. | 524/108 |
| 4,425,328 | 1/1984 | Nabial | 424/68 |
| 4,429,140 | 1/1984 | Murial et al. | 549/370 |
| 4,518,582 | 5/1985 | Schamper et al. | 424/66 |
| 4,639,369 | 1/1987 | Ciaudelli | 424/59 |
| 4,719,102 | 1/1988 | Randhawa et al. | 424/66 |
| 4,722,835 | 2/1988 | Schamper et al. | 424/66 |
| 4,725,430 | 2/1988 | Schamper et al. | 424/66 |
| 4,725,432 | 2/1988 | May | 424/66 |
| 4,743,444 | 5/1988 | McCall | 424/66 |
| 4,781,917 | 11/1988 | Luebbe et al. | 424/65 |
| 4,816,261 | 3/1989 | Luebbe et al. | 424/65 |
| 4,822,602 | 4/1989 | Sabatelli | 424/65 |
| 4,822,603 | 4/1989 | Farris et al. | 424/66 |
| 4,919,934 | 4/1990 | Deckner et al. | 424/402 |
| 4,944,937 | 7/1990 | McCall | 424/65 |
| 4,944,938 | 7/1990 | Potini | 424/68 |
| 4,948,578 | 8/1990 | Burger et al. | 424/68 |
| 4,980,156 | 12/1990 | Raleigh et al. | 424/66 |
| 4,985,238 | 1/1991 | Tanner et al. | 424/66 |
| 4,987,243 | 1/1991 | Kawam et al. | 556/27 |
| 5,019,375 | 5/1991 | Tanner et al. | 424/66 |
| 5,023,354 | 6/1991 | Salome et al. | 549/364 |
| 5,102,656 | 4/1992 | Kasat | 424/66 |
| 5,106,999 | 4/1992 | Gardlik et al. | 549/364 |
| 5,156,834 | 10/1992 | Beckmeyer et al. | 424/47 |
| 5,169,626 | 12/1992 | Tanner et al. | 424/66 |
| 5,200,174 | 4/1993 | Gardlik et al. | 424/66 |
| 5,346,694 | 9/1994 | Juneja | 424/66 |
| 5,384,117 | 1/1995 | Vu et al. | 424/66 |
| 5,429,816 | 7/1995 | Hofrichter et al. | 424/66 |
| 5,449,511 | 9/1995 | Coe | 424/66 |
| 5,455,026 | 10/1995 | Bahr et al. | 424/65 |
| 5,480,637 | 1/1996 | Smith | 424/78.02 |
| 5,486,566 | 1/1996 | Katsoulis | 524/773 |
| 5,492,691 | 2/1996 | Bahr et al. | 404/65 |
| 5,500,209 | 3/1996 | Ross et al. | 424/66 |
| 5,531,986 | 7/1996 | Shevade et al. | 424/68 |
| 5,552,136 | 9/1996 | Motley | 424/68 |

OTHER PUBLICATIONS

Tachibana, Mori and Hori, "Chiral Mesophases of 12–Hydroxyoctadecanoic Acid in Jelly and in the Solid State. II. A new Type of Mesomorphic Solid State", *Bulletin of the Chemical Society of Japan*, vol. 54, 73–80 (1981).

Ito, Yudasaka and Fujtyama, "Light Scattering Study of the 12–Hydroxyoctadecanoic Acid and Benzane Mixture in the Gel State", *Bulletin of the Chemical Society of Japan*, vol. 54, 1939–1942 (1981).

Tamura, Suetake, Ohkubo and Ohbu, "Effect of Alkali Metal Ions on Gel Formation in the 12–Hydroxystearic Acid/Soybean Oil System", *JAOCS*, vol. 71, No. 8 (Aug. 1994).

Cebula and Smith, "Differential Scanning Calorimetry of Confectionery Fats. Pure Triglycerides: Effects of Cooling and Heating Rate Variation", *JAOCS*, vol. 68 No. 8 (Aug. 1991).

Taro Tachibana, Tomoko Mori, and Kayako Hori, "Chiral Mesophases of 12–Hydroxyoctadecanoic Acid in Jelly and in the Solid State. I. A New Type of Lyotropic Mesophase in Jelly with Organic Solvents", *Bulletin of the Chemical Society of Japan*, vol. 53, No. 6, 1714–1719 (1980).

\* cited by examiner

GEL COMPOSITIONS CONTAINING GELLANTS IN THE FORM OF ALKYL AMIDES OF TRI-CARBOXYLIC ACIDS

FIELD OF THE INVENTION

The present invention relates to gel compositions comprising alkyl amides of tri-basic carboxylic acids and methods of making gel compositions.

BACKGROUND OF THE INVENTION

Gelling agents and thickeners are generally regarded as substances added during the manufacturing process to achieve a desired consistency or viscosity. Gelling agents are, typically, added as fluidity modifiers or solidifiers for paints and inks, gelling agents for recovering spilt oils, solidifiers for pesticide formulations, anticlumping agents for paintings or adhesive materials, processing aids for macromolecules as well as gelling agents or solidifiers for perfumes or other cosmetic compositions. Traditional gelling agents include metal salts of stearic acid, clays, pectins, carrageenan, alginates, nylon, fumed silicas, organic derivatives of castor oil and ethyoxylated saturated fatty acids. More recent gelling agents include dibenzylsorbitol and derivatives thereof having a substituent or substituents on the aromatic ring, 12-hydroxystearic acid, acylated amino acid amides and cholesterol derivatives.

While the prior art discloses a wide variety of useful gelling agents, there is still a need for additional gelling agents which provide improved gel stability and/or hardness at reduced manufacturing costs. The present inventors have found that gelling agents in the form of alkyl amides of tri-basic carboxylic acids provide such reduced costs while also providing improved gel stability and/or hardness.

Accordingly, it is an object of the present invention to provide improved gelling agents.

Another object of the present invention is to provide improved gelling agents for formulating stable gel or stick compositions.

These and other objects will become readily apparent from the disclosure which follows.

SUMMARY OF THE INVENTION

The present invention relates to gel compositions, comprising:

A.) a gelling agent of the formula:

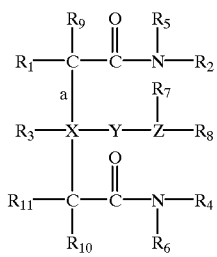

a) $R_1$ is nil, hydroxy, hydrogen, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esthers, $C_1$–$C_{22}$ alkyl ethers, or $C_1$–$C_{22}$ alkyl substituted aryl;
b) $R_2$, $R_4$, $R_5$ and $R_6$ are independently or together, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esthers, $C_1$–$C_{22}$ alkyl ethers, or $C_1$–$C_{22}$ alkyl substituted aryl;
c) $R_3$ is nil, hydroxy, hydrogen, saturated or unsaturated, substituted or unsubstituted, straight, branched or cyclic chain $C_1$–$C_4$ alkyl, $C_1$–$C_4$ alkenyl, $C_1$–$C_4$ alkoxy, $C_1$–$C_4$ alkyl esters or $C_1$–$C_4$ alkyl ethers;
d) $R_7$ and $R_8$ are independently or together, nil, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl;
e) $R_9$ is nil or hydrogen;
f) $R_{10}$ and $R_{11}$ are independently or together, nil, hydrogen, hydroxy, aryl, siloxane or saturated or unsaturated, substituted or unsubstituted, straight, branched or cyclic chain $C_1$–$C_6$ alkyl, $C_1$–$C_6$ alkenyl, $C_1$–$C_6$ alkoxy, $C_1$–$C_6$ alkyl esthers, $C_1$–$C_6$ alkyl ethers, or $C_1$–$C_6$ substituted aryl;
g) X is nitrogen, aryl or —(CH$_2$)—$_n$ where n is an integer from 1 to 6;
h) Y is nil, acyl or carbonyl;
i) Z is nil, hydrogen, hydroxy, aryl, siloxane, nitrogen or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl; and
j) "a" is a double bond or single bond provided:
  (i) when X and Z are not nil and Y is nil, X is directly bonded to Z;
  (ii) when Z is nil, a hydrogen or a hydroxy, $R_7$ and $R_8$ are nil; and
  (iii) when "a" is a double bond, $R_3$ and $R_9$ are nil; and B.) an anhydrous solvent.

The present invention further relates to methods of manufacturing gels.

By "acyl" or "carbonyl" as used herein, means a radical formed by removal of the hydroxy and alkyl portions of a carboxylic acid (i.e.).

By "alkyl" as used herein, means an unsubstituted or substituted saturated hydrocarbon chain radical having from 1 to 22 carbon atoms, preferably from 1 to 8 carbon atoms. Preferred alkyl groups include, but are not limited to, methyl, ethyl, propyl, isopropyl, butyl, octyl and hexyl.

By "alkenyl" as used herein, means an unsubstituted or substituted hydrocarbon chain radical having from 2 to 22 carbon atoms, preferably from 2 to 8 carbon atoms, and having at least one olefinic double bond.

By "aryl" as used herein, means an aromatic carbocyclic ring radical. Preferred aryl groups include, but are not limited to, phenyl, tolyl, xylyl, cumenyl and naphthyl.

By "alkoxy" as used herein, means an oxygen radical having a hydrocarbon chain substituent, where the hydrocarbon chain is an alkyl or alkenyl (i.e., —O—alkyl or —O—alkenyl). Preferred alkoxy groups include, but are not limited to, methoxy, ethoxy, propoxy and allyloxy.

By "siloxane" as used herein, means a linear compound consisting of silicon atoms single-bonded to oxygen and so arranged that each silicon atom is linked with two or four oxygen atoms (i.e., —Si(O)$_2$RR' where R and R', independently, are, but not limited to, alkyls, alkyl esters or alkyl ethers).

By "cyclic chain" as used herein, means an unsubstituted or substituted, saturated, unsaturated or aromatic, hydrocarbon chain ring radical. The cyclic chains are monocyclic or are fused, bridged or spiro polycyclic ring systems.

As defined above and as used herein, substituent groups may themselves be substituted. Such substitution may be with one or more substituents. Such substituents include (for example) those listed in C. Hansch and L. Leo, *Substituent Constants for Correlation Analysis in Chemistry and Biology* (1979), incorporated by reference herein. Preferred substitients include (for example) alkyl, alkenyl, alkoxy, hydroxy, oxo, nitro, amino, aminoalkyl (e.g. aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

All levels and ratios are by weight of the total composition, unless otheriwse indicated. By the phrase "ambient temperature" as used herein, refers to surrounding conditions under about one atmosphere of pressure, at about 50% relative humidity, and at about 25° C., unless otherwise specified.

The gel compositions of the present invention can comprise, consist of, or consist essentially of the essential elements and limitations of the invention described herein, as well as any of the additional or optional ingredients, components, or limitations described herein.

DETAILED DESCRIPTION OF THE INVENTION

The essential as well as optional components of the compositions of the present invention are described in the following paragraphs.

ESSENTIAL COMPONENTS

Alkyl Amides of Di- and/or Tri-basic Carboxylic Acids

An essential component of the present invention are gelling agents in the form of alkyl amides of tri-basic carboxylic acids or anhydrides. Alkyl amides suitable for use in the present invention generally have the formula:

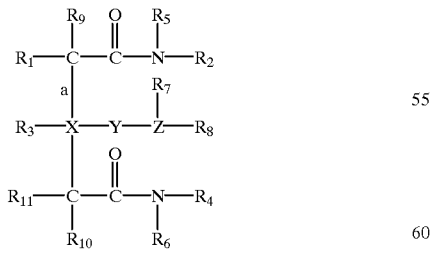

wherein a backbone is formed from the linkage of C', C" and X and wherein a) $R_1$ is nil, hydroxy, hydrogen, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{18}$ alkyl, $C_4$–$C_{18}$ alkenyl, $C_4$–$C_{18}$ alkoxy, $C_4$–$C_{18}$ alkyl esters, $C_4$–$C_{18}$ alkyl ethers, or $C_4$–$C_{18}$ alkyl substituted acyl, more preferably $C_{12}$–$C_{18}$ alkyl, $C_{12}$–$C_{18}$ alkenyl, $C_{12}$–$C_{18}$ alkoxy, $C_{12}$–$C_{18}$ alkyl esters, $C_{12}$–$C_{18}$ alkyl ethers, or $C_{12}$–$C_{18}$ alkyl substituted aryl;

b) $R_2$, $R_4$, $R_5$ and $R_6$ are independently or together, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

c) $R_3$ is nil, hydroxy, hydrogen, saturated or unsaturated, substituted or unsubstituted, straight, branched or cyclic chain $C_1$–$C_4$ alkyl, $C_1$–$C_4$ alkenyl, $C_1$–$C_4$ alkoxy, $C_1$–$C_4$ alkyl esters or $C_1$–$C_4$ alkyl ethers, preferably a $C_1$–$C_4$ alkoxy, hydroxy or hydrogen, more preferably a hydroxy or hydrogen;

d) $R_7$ and $R_8$ are independently or together, nil, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

e) $R_9$ is nil or hydrogen;

f) $R_{10}$ and $R_{11}$ are independently or together, nil, hydrogen, hydroxy, aryl, siloxane or saturated or unsaturated, substituted or unsubstituted, straight, branched or cyclic chain $C_1$–$C_6$ alkyl, $C_1$–$C_6$ alkenyl, $C_1$–$C_6$ alkoxy, $C_1$–$C_6$ alkyl esters, $C_1$–$C_6$ alkyl ethers, or $C_1$–$C_6$ alkyl substituted aryl, preferably $C_1$–$C_4$ alkyl, $C_1$–$C_4$ alkenyl, $C_1$–$C_4$ alkoxy, $C_1$–$C_4$ alkyl esters, $C_1$–$C_4$ alkyl ethers, $C_1$–$C_4$ alkyl substituted aryl or hydrogen, more preferably a hydrogen;

g) X is nitrogen, aryl or —(CH$_2$)$_n$— where n is an integer from 1 to 6, preferably —(CH$_2$)$_n$— where n is an integer from 1 to 3;

h) Y is nil, acyl or carbonyl;

i) Z is nil, hydrogen, hydroxy, aryl, siloxane, nitrogen or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl; and j) "a" is a double or single bond provided:
(i) when X and Z are not nil and Y is nil, X is directly bonded to Z;

(ii) when Z is nil, a hydrogen or a hydroxy, $R_7$ and $R_8$ are nil; and (iii) when "a" is a double bond, $R_3$ and $R_9$ are nil.

Alkyl amides of tri-basic carboxylic acids suitable for use in the present invention include, but are not limited to, alkyl amides of citric acid, tricarballylic acid, aconitirc acid, nitrolotriacetic acid and itaconic acid such as 1,2,3-propane tributylamide, 2-hydroxy-1,2,3-propane tributylamide, 1-propene-1,2,3-trioctylamide, and N,N',N"-tri (acetodecylamide)amine.

The alkyl amide gelling agents, preferably, have opposing and substantially parallel terminal chains extending outward from the gelling agent backbone. Without being limited by theory, it is believed that this spacial arrangement, or "tuning fork" structural configuration, facilitates the formation of networks essential to the formulation of gel or stick compositions. By the phrase "tuning fork configuration", as used herein means any configuration resembling an article or implement having a handle portion which extends longitudinally at one end to form two prongs. It is also preferred that the terminal chains be linked to the gelling agent backbone by means of acyl-amide linkages wherein the acyl portion of the acyl-amide linkage is directly attached to the gelling agent backbone.

The alkyl amides of the present invention are synthesized using either of the following one or two step reaction procedures.

The one step procedure involves direct amidation of the tri-basic organic acid or anhydride with the appropriate alkyl amine under reaction temperatures typically at or near the boiling point of the alkyl amine, preferably from about 30° C. to about 200° C., followed by removal of excess amine. Certain reactions, do to their exothermic nature, may not require external heating.

The two step procedure involves esterification of the tri-basic organic acid or anhydride with methanol using a boron trifluoride or other Lewis Acid catalyst at a temperature of from about 30° C. to about 100° C. followed by removal of the excess methanol and catalyst. The resulting trimethyl ester is then amidated as described in the one step process above using the appropriate alkylamide followed by removal of excess amine. Preferably, the alkyl amides of the present invention are nonpolymeric.

When the alkylamide of the present invention is included at lower levels in the composition, a gel is formed. At higher levels, or when other gelling agents are included in the composition, the hardness of the composition is increased, so as to form a hard stick. The alkyl amides of tri-basic carboxylic acids are preferably present at a concentration of from about 0.1% to about 50%, preferably about 0.1% to about 25% from more preferably from about 1% to about 16%.

Anhydrous Solvent

The gels of the present invention further comprise an anhydrous solvent for solubilizing the tri-basic carboxylic acid alkyalmide gelling agent, wherein the solvent comprises one or more anhydrous liquids which each or collectively have a solubility parameter of from about 3 to about 20 $(cal/cm^3)^{1/2}$, preferably from about 5 to about 16 $(cal/cm^3)^{1/2}$, more preferably from about 5 to about 11 $(cal/cm^3)^{1/2}$. The solvent is a liquid under ambient conditions.

Solubility parameters for the liquid solvents or other materials, and means for determining such parameters, are well known in the chemical arts. A description of solubility parameters and means for determining them are described by C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J. Soc. Cosmetic Chemists 319–333, September/October, 1988, which descriptions are incorporated herein by reference.

Concentrations of the solvent in the gel will vary with the type of solvent selected, the type of gelling agent used in combination with the solvent, and the solubility of the selected gelling agent in the selected solvent, and so forth. Preferred concentrations of the solvent ranges from about 10% to about 99.9%, preferably from about 30% to about 70%, more preferably from about 45% to about 70%, by weight of the composition.

The solvent preferably comprises one or more anhydrous liquid solvents suitable for topical application to human skin, which solvent or combination of liquid solvents are liquid under ambient conditions. The term "anhydrous" as used herein means that the gel composition of the present invention, and the essential or optional components thereof are substantially free of added or free water. From a formulation standpoint, this means that the gel composition of the present invention preferably contain less than about 5%, preferably less than about 3%, more preferably less than about 1%, most preferably zero percent, by weight of free or added water. These liquid anhydrous, solvents may be organic or silicone-containing, volatile or non-volatile, polar or nonpolar, provided that the solvent can form a solution or other homogenous liquid or homogenous liquid dispersion with the selected gellant at the selected gellant concentration at a temperature of from about 28° C. to about 250° C., preferably from about 28° C. to about 100° C., more preferably from about 28° C. to about 78° C. The anhydrous liquid solvent preferably has a low viscosity to provide for improved spreading performance on the skin.

The anhydrous liquid solvent preferably comprises a modified or organofunctional silicone solvent selected from the group consisting of polyalkylsiloxanes, polyalkarylsiloxanes, polyestersiloxanes, polyethersiloxane copolymers, polyfluorosiloxanes, polyaminosiloxanes, and combinations thereof. These modified silicone solvents must be liquid under ambient conditions, and have a viscosity of less than about 100,000 centistokes, preferably less than about 500 centistokes, more preferably from about 1 centistoke to about 50 centistokes, and even more preferably from about 1 centistoke to about 20 centistokes. These modified solvents are generally known in the chemical arts, some example of which are described in 1 *Cosmetics, Science and Technology* 27–104 (M. Balsam and E. Sagarin ed. 1972); U.S. Pat. No. 4,202,879, issued to Shelton on May 13, 1980; U.S. Pat. No. 5,069,897, issued to Orr on Dec. 3, 1991; which descriptions are incorporated herein by reference.

The modified silicone solvents for use in the pharmaceutical compositions include, but are not limited to, compounds or materials as defined hereinabove and which are generally characterized as follows: silicone polyethers or silicone glycols (such as dimethicone copolyol); silicone alkyl-linked polyethers (such as Goldschmidt EM-90 or EM-97); siloxane surfactants of a pendant/rake/comb configuration, silicone surfactants of a trisiloxane configuration, and silicone surfactants of an ABA/alpha-omega block copolymers (such as polyoxyalkylenes, polyoxyethylene or ethyoxylated, polyoxyethylene/polyoxypropylene or ethoxylated/propoxylated); aromatic substituted silicone emollients (such as phenyl, alpha-methyl styryl, styryl, methylphenyl, alkylphenyl); silicone copolymers with other functional groups include: hydrogen, alkyl, methyl, aminio, trifluoropropyl, vinyl, alkoxy, aryalkyl, aryl, phenyl, styryl, polyethers, esters, carboxylics; alkylmethyl siloxanes or silicone waxes (such as hexyl, octyl, lauryl, cetyl, stearyl); nonionic functional siloxane copolymers with terminal groups being silanol or trimethylsiloxy; nonionic functional siloxanes with backbone groups being trisiloxane or methicone linked; nonionic silicone surfactants; tetraethoxysilane; tetramethoxysilane; hexamethoxysilicone; oxmethoxytrisiloxane; silicone emulsifiers; silicone or siloxane resins, alkyl silicone resins, polyoxyalkylene silicone resins; MQ Resins such as Shiseido/Shin-etsu, e.g. Japanese Patent Publication JP86143760 or from Walker Chem. 6MBH (described in EP722970); alkoxysiloxanes; alkoxysilanes; methicones (polymethylalkylsiloxanes); and combinations thereof.

Nonlimiting examples of suitable modified silicone solvents for use in the pharmaceutical compositions herein include the following modified silicones available from Dow Corning: DC-556 Cosmetic Grade Fluid (phenyl trimethicone); DC-704 Diffusion Pump Fluid (Tetramethyl-Tetraphenyl-Trisiloxane); DC-705 Diffusion Pump Fluid; DC-1784 Emulsion; DC-AF Emulsion; DC-1520-US Emulsion; DC-593 Fluid (Dimethicone [and] Trimethylsiloxysilicate); DC-3225C Fluid (Cyclomethicone [and] Dimethicone Copoly); DC-190 Fluid (Dimethicone Copoly); DC-193 Fluid (Dimethicone Copolyol); DC-1401 (Cyclomethicone [and] Dimethiconol); DC-5200 Fluid (Laurylmethicone Copolyol); DC-6603 Polymer Powder; DC-5640 Powder; DC-Q2-5220 (Dimethicone Copolyol); DC Q2-5324 (Dimethicone Copolyol); DC-250 Cosmetic Wax (Dimethicone Copolyol); DC-2502 Fluid (Cetyl Dimethicone); DC-2503 Wax (Stearyl Dimethicone); DC-1731 Volatile Fluid (Caproyl Trimethicone); DC-580 Wax (Stearoxytrimethylsilane [and] Stearyl Alcohol); DC-1-3563 (Dimethiconal); DC-X2-1286 (Dimethiconol); DC-X2-1146A (Cyclomethicone [and] Dimethiconol); DC-8820 Fluid (Amino functionalized); DC Q5-0158A wax (stearoxytrimethylsilane); DC-Q2-8220 (Trimethylsilyamodimethicone); DC-7224 (Trimethylsilyamodimethicone); DC-X2-1318 Fluid (Cyclomethicone [and] Vinyldimethicone); DC-QF1-3593A fluid (Trimethylsiloxysilicate) and combinations thereof.

Other nonlimiting examples of suitable modified silicone solvents for use in the pharmaceutical compositions herein include the following modified silicones available from General Electric: GE SF-1023 (Dimethyl-Diphenyl-Siloxane); GE CF-1142 (Methylphenyl Siloxane Fluid); GE SF-1153 (Dimethyl-Diphenyl-Siloxane); GE SF-1265 (Diphenyl-Dimethyl-Siloxane); GE SF-1328; GE SF-1188 (Dimethicone copolyol); GE SF-1188A (Silicone polyether copolymer); GE SF-1288 (silicone polyether copolymer, dimethyl-methyl-3-hydroxypropyl ethoxylated); GE SF-1318 (Methylester Siloxane); GE SF-1328 (silicone surfactant, dimethyl-methyl 3-hydroxypropyl ethoxylated-propoxylated); GE SF-1550 (methylphenyl siloxane, hexamethyl-3-phenyl-3-[[trimethylsily]oxy]trisiloxane); GE SF-1632 (silicone wax); GE SS-4267 (Dimethicone [and] Trimethylsiloxysilicate.

Other nonlimiting examples of suitable modified silicone solvents for use in the pharmaceutical compositions herein include the following modified silicones available from Goldschmidt; Abil EM-90 (silicone emulsifier); Abil EM-97 (polyether siloxane); Abil Wax 9810 (silicone wax or C24-28 methicone); Abil Wax 2434 (Stearoxy Dimethicone); Abil Wax 9800D (Stearyl Dimethicone); and Tegomer H-Si 2111, H-Si 2311, A-Si 2120, A-Si 2320, C-Si 2141, C-Si 2341, E-Si 2130, E-Si 2330, V-Si 2150, V-Si 2550, H-Si 6420, H-Si 6440, H-Si 6460 (Alpha-Omega Dimethicone Copolymers).

Other nonlimiting examples of suitable modified silicone solvents for use in the pharmaceutical compositions herein include the following: Masil 756 from PPG Industries (Tetrabutoxypropyl Trisiloxane); bis-phenylhexamethicone (available as Silbione Oils 70633 V30 from Rhone-Poulenc); Sibione Oils 70646 (dimethicone copolyols from Rhone-Poulenc); Silicone L-711, L-720, L-721 and L-722 (dimethicone copolyols from Union Carbide); Silicone L-7000, L-7001, L-7002, L-7004, L-7500, L-7600, L-7602, L-7604, L-7605, and L-7610 (dimethicone copolyols from Union Carbide); Unisil SF-R (dimethiconol from UPI); Silicate Cluster from Olin (Tris[tributoxysiloxy] methylsilane); silicone copolymer F-754 (dimethicone copoly from SWS Silicones); and combinations thereof.

The anhydrous liquid solvent preferably comprises one or more volatile solvents, optionally in combination with one or more non-volatile solvent. In this context, the term "volatile" refers to solvents having a measurable vapor pressure under ambient conditions, and the term "non-volatile" refers to solvents which do not have a measurable vapor pressure under ambient conditions. These volatile silicone solvents may be cyclic, linear or branched chain silicones having the requisite volatility defined herein. Non-limiting examples of suitable volatile silicones are described in Todd et al., "Volatile Silicone Fluids for Cosmetics", Cosmetics and Toiletries, 91:27–32 (1976), which descriptions are incorporated herein by reference. Preferred among these volatile silicones are the cyclic silicones having from about 3 to about 7, more preferably from about 4 to about 5, silicon atoms. Most preferably are those which conform to the formula:

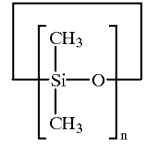

wherein n is from about 3 to about 7, preferably from about 4 to about 5, most preferably 5. These volatile cyclic silicones generally have a viscosity value of less than about 10 centistokes. All viscosity values described herein are measured or determined under ambient conditions, unless otherwise specific. Suitable volatile silicones for use herein include, but are not limited to, Cyclomethicone D-5 (commercially available from G. E. Silicones); Dow Corning 344, and Dow Corning 345 (commercially available from Dow Corning Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

The anhydrous liquid solvent may also comprise a non-volatile silicone solvent other than or in addition to the preferred modified silicone solvents described hereinbefore. These non-volatile silicone solvents are preferably linear silicones which include, but are not limited to, those which conform to either of the formulas:

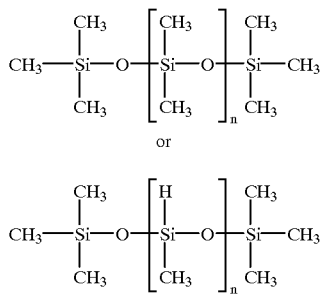

or wherein n is greater than or equal to 1. These linear silicone materials will generally have viscosity values of up to about 100,000 centistoke, preferably less than about 500 centistoke, more preferably from about 1 centistoke to about 200 centistoke, even more preferably from about 1 centistoke to about 50 centistoke, as measured under ambient conditions. Examples of non-volatile, linear silicones suitable for use in the antiperspirant compositions include, but are not limited to, Dow Corning 200, hexamethyldisiloxane, Rhodorsil Oils 70047 avaiable from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G. E. Silicones); Velvasil and Viscasil (available from General Eletric Co.); and Silicone L-45, Silicone L530, Silicone L-531 (available from Union Carbide), and Siloxane F-221 and Silicone Fluid SWS-101 (available from SWS Silicones).

The anhydrous liquid solvent may also comprise fluorochemcials such as fluorosurfactants, fluorotelemers, and perfluoropolyethers, some examples of which are described in Cosmetics & Toiletries, Using Fluorinated Compounds in Topical Preparations, Vol. 111, pages 47–62, (Oct. 1996) which description is incorporated herein by reference. More specific examples of such liquid solvents include, but are not limited to, perfluoropolymethyl isopropyl ethers, perfluoropolypropylethers, acrylamide fluorinated telomer, fluorinated amide surfactants, perfluorinated thiol surfactants. Other more specific examples include, but are not limited to, the polyperfluoroisoproyl ethers available from Dupont Performance Chemicals under the trade name Fluortress® PFPE oils, and the series fluorosurfactants from Dupont Performance Chemicals under the trade name Zonyl® Fluorosurfactants.

Suitable organic liquid solvents for use in the composition include saturated or unsaturated, substituted or unsubstituted, branched or linear or cyclic, organic compounds that are also liquid under ambient conditions. These solvents include hydrocarbon oils, alcohols, organic esters and ethers that are liquid under ambient conditions. Preferred organic solvents include mineral oil and other hydrocarbon oils, some examples of which are described in U.S. Pat. No. 5,019,375, issued to Tanner et al. on May 28, 1991, which description is incorporated herein by reference. Other suitable organic liquid solvents include Permethyl 99A, Permethyl 101A (Permethyl available from Persperse Corp.), Isopar series of materials (available from Exxon), isohexadecane, diisopropyl adipate, butyl stearate, isododecane, light mineral oil, petrolatum and other similar materials.

The anhydrous liquid solvent is preferably, substantially free of polar, water immiscible, organic solvents. In this context, "substantially free" means that the gel solid compositions preferably contain less than 7%, more preferably less than about 3%, even more preferably zero percent, by weight of an anhydrous organic polar solvent. These solvents are liquid under ambient conditions and include mono and polyhydric alcohols, fatty acids, esters of mono and dibasic carboxylic acids with mono and polyhydric alcohols, polyoxyethylenes, polyoxypropylenes, polyalkoxylates ethers of alcohols, and combinations thereof. Examples of some anhydrous liquid, polar organic solvents are described in Cosmetics, Science, and Technology, Vol. 1, 27–104, edited by Balsam and Sagarin (1972); U.S. Pat. No. , 4,202,879 issued to Shelton on May 13, 1980; and U.S. Pat. No. 4,816,261 issued to Luebbe et al. on Mar. 28, 1989, which descriptions are incorporated herein by reference.

Product Characteristics

The gel compositions of the present invention are preferably characterized in terms of product hardness, and/or a rheology profile defined by a ratio of an elastic to viscous moduli. Each of these characteristics is defined in accordance with the methodologies and other limitations described hereinafter.

a) Hardness

The gel compositions of the present invention preferably have a product hardness of from about 500 gram force to about 5000 gram force, more preferably from about 750 gram force to about 2,000 gram force, and most preferably from about 800 gram force to about 1400 gram force.

The term "product hardness" as used herein is a reflection of how much force is required to move a penetration cone a specified distance and at a controlled rate into a gel-solid stick composition under the following test conditions. Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the amount of force required to move a standard 45° angle penetration cone through the composition for a distance of 10 mm at a rate of 2 mm/second. The standard cone is avaiable from Texture Technology Corp., as part number TA-15, and has a total cone length of about 24.7 mm, angled cone length of about 18.3 mm, a maximum diameter of the angled surface of the cone of about 15.5 mm. The cone is a smooth, stainless steel construction and weighs about 17.8 grams.

c) Rheology

The gel compositions of the present invention are preferably gel-solids having the select rheology profile defined herein. This rheology is defined herein in terms of the elastic (G') to viscous (G") moduli ratio (G'/G") of the gel-solid stick composition. To provide the desired rheology, the gel compositions preferably have a G'/G" ratio of from about 1 to about 100, more preferably from about 1 to about 70, most preferably from about 1 to about 20, even more preferably from about 1 to about 10. This ratio represents the extent to which the gel compositions herein are preferred to exhibit solid character and the extent to which the compositions are preferred exhibit liquid or fluid character, and specifically refers to the numerical ratio G'/G" as determined by the following methodology.

In particular, the elastic modulus is a measurement which correlates with the solid character of the gel compositions herein, and the viscous modulus is a measurement which correlates with the fluid or liquid character of the gel compositions herein.

Measurements for G' and G" for purpose of defining the composition of the present invention are determined under ambient conditions using conventional techniques well known in the formulation arts. For example, a Bohlin Stress-Strain Rheometer, available from Bohlin Reologi, Cranberry, N.J., can be used using a cone (about 1°) and plate configuration. About 1.0 mg of the product is carefully removed for the composition with minimal application of shear force and is then placed between the cone and plate fixtures for measurement of G' and G".

OPTIONAL COMPONENTS

In addition to the alkylamide gelling agent described above, the compositions of the present invention may also incorporate other gelling agents. Suitable additional gelling agents are disclosed in U.S. Pat. No. 5,429,816 to Hofrichter et al., issued Jul. 4, 1995, herein incorporated by reference in its entirety. Gelling agents included therein include those having the formula:

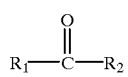

wherein $R_1$ is $OR_2$ or $NR_2R_3$ wherein $R_2$ and $R_3$ are, independently or together, a hydrogen, an aryl, a siloxane, a saturated or unsaturated, substituted or unsubstituted, straight, branched, or cyclic $C_1$–$C_{22}$ alkyl, $CV_1$–$C_{22}$ alkoxy, $C_1$–$C_{22}$ alkyl substituted aryl, or $C_1$–$C_{22}$ alkyl substituted aryl radical and wherein $R_2$ is a saturated or unsaturated, substituted or unsubstituted, straight or branched chain $C_1$–$C_{36}$ alkoxy. Preferred gelling agents from among this group include 12-hydroxystearic acid, 12-hydroxystearic acid methyl ester, 12-hydroxystearic acid ethyl ester, 12-hydroxystearic acid stearyl ester, 12-hydroxystearic acid benxyl ester, 12-hydroxystearic acid amide, isopropyl amide of 12-hydroxystearic acid, butyl amide of 12-hydroxystearic acid, benxyl amide of 12-hydroxystearic acid, phenyl amide of 12-hydroxystearic acid t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, 12-hydroxylauric acid, 16-hydroxyhexadecanoic acid, derivatives thereof and mixtures thereof.

Also in U.S. Pat. No. 5,429,816 are gelling agents having the formula:

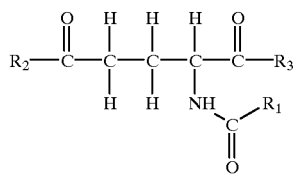

wherein $R_1$ is an alkyl, aryl, arylalkyl radical, is branched, linear or cyclic and has from about 6 to about 22 carbon atoms; and $R_2$ and $R_3$ are the same or different alkyl, aryl, arylalkyl ester radical or alkyl, aryl, arylalkyl amide radical, in which the moiety is branched, linear or cyclic and has from about 2 to about 20 carbon atoms. Preferred gelling agents from among this group include N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl asmide, N-stearoyl-glutamic acid dididecyl amide, N-stearoyl-glutamic acid ditetradecyl amide, N-stearoyl-glutamic acid dihexadecyl amide, N-stearoyl-glutamic acid distearyl amide and mixtures thereof. Mixtures of the above described additional gelling agents may also be incorporated into the present invention.

The gel compositions of the present invention may also be formulated into cosmetic compositions optionally include cosmetic actives such as moisturizers and/or skin protectants. Suitable cosmetic compositions include lipsticks gels, bar soaps, lip balms, soft gels, creams, makeups, lotions, roll-ons, facial moisturizers, or gel sticks and the like. Useful moisturizers and/or skin protectants are disclosed in the *Federal Register* Vol. 48, No 32 and include aloe vera, allantoin, aluminum hydroxide gel, bismuth subnitrate, boric acid, calamine, cocoa butter, corn starch, dimethicone, glycerin, lanolin, kaolin, live yeast cell derivative, petrolatum, shark liver oil, sodium bicarbonate, sulfur, tannic acid, white petrolatum, zinc acetate, zinc carbonate and zinc oxide and mixtures thereof. The skin protectant and/or moisturizer preferably comprise from about 0.001% to about 2%, more preferably from about 0.01% to about 1% of the gel composition.

Mixtures of these gelling agents may also be incorporated into the present invention.

METHODS OF MANUFACTURE

The present invention may be made by using any of the typical method known to those skilled in the art. Methods found particularly useful follow below:

Combine the gelling agent and the solvent into a vessel equipped with a heat source. Heat the mixture to between about 80° C. and about 130° C. with stirring, until the mixture forms a homogeneous, molten solution. Preferably, the homogeneous, molten solution is allowed to cool to a mixing temperature; typically between about 65° C. and 120° C. Alternatively, the mixture may simply be heated to the mixing temperature until the moisture forms a homogeneous, molten solution. This alternative method, however, typically takes longer than simply overheating and then cooling. Allow the mixture to cool until it begins thickening and then pour the mixture into containers allowing them to cool to ambient temperature.

EXAMPLES

The following examples further describe and demonstrate embodiments within the scope of the present invention. These examples are solely for the purpose of illustration and are not to be construed as limitations of the present invention as many variations are possible without departing from the spirit or scope thereof. The levels of the components in the examples below are expressed by total weight of the composition.

Table 1 includes Examples of gel solid stick compositions incorporating the alkylamide gelling agents of the present invention. The compositions are formed by combining and mixing the ingredients of each column using conventional technology.

TABLE 1

| Component | Example I | Example II | Example III | Example IV | Example V |
|---|---|---|---|---|---|
| Cyclomethicone[1] | 72.0 | 70.0 | 46.0 | 64.0 | 30.0 |
| Octyldodecanol[2] | 18.0 | 18.0 | 14.0 | — | — |
| Petrolatum[3] | — | — | — | — | 55.0 |
| $C_{12}$–$C_{15}$ Alkyl Benzoate[5] | — | — | — | 20.0 | — |
| 12-Hydroxystearic Acid[4] | — | — | — | 13.0 | — |
| 1,2,3-Propane tributylamide | 10.0 | 5.0 | — | — | 15.0 |
| 2-Hydroxy-1,2,3-propane tributylamide | — | 5.0 | 25.0 | — | — |
| 1-Propene-1,2,3-trioctylamide | — | — | — | 3.0 | — |
| Glycerin | — | 2.0 | — | — | — |
| Allantoin | — | — | 2.0 | — | — |
| Hardness (gram-Force) | 1252 | 1250 | 4000 | 2050 | 2500 |

[1] Dow Corning 245 Fluid; General Electric SF-1202
[2] Jarchem Jarcol I-20
[3] Witco White Perfecta
[4] Acme Hardesty
[5] Finsolv TN; Finetex Table 2 includes Examples of soft gel compositions incorporating the alkylamide gelling agents of the present invention. The compositions are formed by combining and mixing the ingredients of each column using conventional technology.

TABLE 2

| Component | Example VI | Example VII | Example VIII | Example IX | Example X |
|---|---|---|---|---|---|
| Cyclomethicone[1] | 81.0 | 79.0 | 76.0 | 76.0 | — |
| Octyldodecanol[2] | 18.0 | 18.0 | — | 20.0 | — |
| Petrolatum[3] | — | — | — | — | — |
| $C_{12}$–$C_{15}$ Alkyl Benzoate[5] | — | — | 20.0 | — | — |
| 12-Hydroxystearic Acid[4] | — | — | — | 3.0 | — |
| Diethyl Pthalate | — | — | — | — | 99.0 |
| 1,2,3-Propane tributylamide | 1.0 | 0.5 | — | — | 1.0 |
| 2-Hydroxy-1,2,3-propane tributylamide | — | 0.5 | 2.0 | — | — |
| 1-Propene-1,2,3-trioctylamide | — | — | — | 1.0 | — |
| Glycerin | — | 2.0 | — | — | — |
| Allantoin | — | — | 2.0 | — | — |
| Hardness (gram-Force) | 100 | 100 | 100 | 200 | 40 |

[1] Dow Corning 245 Fluid; General Electric SF-1202
[2] Jarchem Jarcol I-20
[3] Witco White Perfecta
[4] Acme Hardesty
[5] Finsolv TN; Finetex

What is claimed is:

1. A gel comprising:

A.) a triamide gelling agent having the formula:

$$R_1-\underset{a}{\overset{R_9}{C'}}-\overset{O}{\overset{\|}{C}}-\underset{}{\overset{R_5}{N}}-R_2$$
$$R_3-X-Y-Z-R_8 \quad (R_7)$$
$$R_{11}-\overset{}{C''}-\overset{O}{\overset{\|}{C}}-\underset{R_6}{\overset{}{N}}-R_4 \quad (R_{10})$$

a) $R_1$ is hydrogen;
b) $R_2$ is saturated or unsaturated, substituted or unsubstituted, straight, branched or cyclic chain $C_1$–$C_{22}$ alkyl, $R_4$ is saturated or unsaturated, substituted or unsubstituted, straight, branched or cyclic chain $C_1$–$C_{22}$ alkyl, $R_5$ and $R_6$ are independently or together, hydrogen;
c) $R_3$ is hydroxy;
d) $R_7$ is hydrogen and $R_8$ is saturated or unsaturated, substituted or unsubstituted, straight, branched or cyclic chain $C_1$–$C_{22}$ alkyl;
e) $R_9$ is hydrogen;
f) $R_{10}$ and $R_{11}$ are independently or together, hydrogen;
g) X is nitrogen, aryl or —(CH$_2$)—$_n$ where n is an integer from 1 to 6;
h) Y is carbonyl;
i) Z is nitrogen;
j) "a" is a single bond; and C.) an anhydrous liquid carrier.

2. A gel according to claim 1 further comprising from about 1% to about 15% by weight of a secondary gelling agent having the formula:

$$R_1-\overset{O}{\overset{\|}{C}}-R_2$$

wherein $R_1$ is $OR_2$ and wherein $R_2$ is a saturated or unsaturated, substituted or unsubstituted, straight or branched chain $C_1$–$C_{36}$ alkoxy.

3. A gel according to claim 2, wherein the gel comprises from about 5% to about 50% of the gelling agent.

4. A gel according to claim 1, wherein the gelling agent is selected from the group consisting of alkyl amides of citric acid, tricarballylic acid, aconitric acid, nitrilotriacetic acid.

5. A gel according to claim 4, wherein the secondary gelling agent is selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl esther, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12- hydroxystearic acid, 1-adamantyl amide of 12-hydroxystearic acid, 2-adamantyl amide of 12-hydroxystearic acid, diisopropyl amide of 12-hydroxystearic acid, 12-hydroxylauric acid, 16-hydroxyhexadecanoic acid, derivatives thereof and mixtures thereof.

6. A gel according to claim 5, further comprising an additional gelling agent having the formula:

$$R_2-\overset{O}{\overset{\|}{C}}-\underset{H}{\overset{H}{C}}-\underset{H}{\overset{H}{C}}-\underset{\underset{\underset{O}{\overset{\|}{C}}}{NH}}{\overset{H}{C}}-\overset{O}{\overset{\|}{C}}-R_3$$
$$\qquad\qquad\qquad R_1$$

wherein $R_1$ is an alkyl and has from about 6 to about 22 carbon atoms; and $R_2$ and $R_3$ are each arylalkyl amide radical, in which the moiety is branched, linear or cyclic and has from about 2 to about 20 carbon atoms.

7. A gel according to claim 6, wherein the additional gelling agent is selected from the group consisting of N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearol-glutamic acid dibutyl amide, N-stearyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-glutamic acid distearyl amide and mixtures thereof.

8. A gel according to claim 1 wherein the solvent is an anhydrous liquid.

9. A gel according to claim 8 wherein the solvent has a solubility parameter of from about 3 to about 20 $(cal/cm^3)^{1/2}$.

10. A gel according to claim 9 wherein the solvent is selected from the group consisting: of nonpolar, volatile oils; relatively polar, non-volatile oils; nonpolar, non-volitale oils; and mixtures thereof.

11. A gel according to claim 10 wherein the nonpolar, volative oils are selected from the group consisting of non-volatile polysiloxanes, paraffinic hydrocarbon oils, and mixtures thereof.

12. A gel according to claim 11 wherein the non-volatile polysiloxanes are selected from the group consisting of polyalkylsiloxanes, polyarylsiloxanes, polyalkylarylsiloxanes, polyethersiloxane copolymers and mixtures thereof.

13. A gel according to claim 11, wherein the paraffinic hydrocarbon oil is selected from the group consisting of mineral oils, petrolatums, isodecanes, permethyls, isohexadecanes, isododecane, isoparaffins.

14. A gel according to claim 11 in the form of a cosmetic composition.

15. A gel according to claim 14 wherein the cosmetic composition is in the form of a lipstick, gel, bar soap, lip balm, soft gel, cream, lotion, roll-on, makeup, facial moisturizer, or gel stick.

16. A gel according to claim 15 further comprising a moisturizer or protectant.

17. A gel according to claim 16 wherein the moisturizer or protectant is selected from the group consisting of aloe vera, allontoin, aluminum hydroxide gel, bismuth subnitrate, boric acid, calamine, cocoa butter, corn starch, dimethicone, glycerin, lanolin, kaolin, live yeast cell derivative, petrolatum, shark liver oil, sodium bicarbonate, sulfur, tannic acid, white petrolatum, zinc acetate, zinc carbonate and zinc oxide and mixtures thereof.

18. A method of forming a gel comprising the steps of:

A) providing a gel forming solvent; and

B) dissolving in the gel forming solvent a triamide gelling agent of the formula:

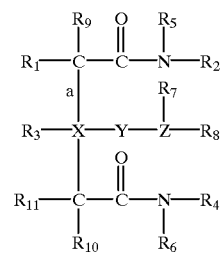

a) $R_1$ is hydrogen;
b) $R_2$ is saturated or unsaturated, substituted or unsubstituted, straight, branched or cyclic chain $C_1$–$C_{22}$ alkyl, $R_4$ is saturated or unsaturated, substituted or unsubstituted, straight, branched or cyclic chain $C_1$–$C_{22}$ alkyl, $R_5$ and $R_6$ are independently or together, hydrogen;
c) $R_3$ is hydroxy;
d) $R_7$ is hydrogen and $R_8$ is saturated or unsaturated, substituted or unsubstituted, straight, branched or cyclic chain $C_1$–$C_{22}$ alkyl;
e) $R_9$ is hydrogen;
f) $R_{10}$ and $R_{11}$ are independently or together, hydrogen;
g) X is nitrogen, aryl or —$(CH_2)$—$_n$ where n is an integer from 1 to 6;
h) Y is carbonyl;
i) Z is nitrogen; and
j) "a" is a single bond; and C) an anhydrous liquid carrier.

* * * * *

UNITED STATES PATENT AND TRADEMARK OFFICE
CERTIFICATE OF CORRECTION

PATENT NO. : 6,190,673 B1
DATED : February 20, 2001
INVENTOR(S) : G.J. Guskey et al.

It is certified that error appears in the above-identified patent and that said Letters Patent is hereby corrected as shown below:

Column 14,
Line 40, "esther" should read -- ester --.

Column 15,
Line 7, "N-stearol-glutamic" should read -- N-stearoyl-glutamic --.
Line 8, "N-stearyl-glutamic" should read -- N-stearoyl-glutamic --.
Line 22, "non-volitale" should read -- non-volatile --.

Column 16,
Line 1, "allontoin" should read -- allantoin --.
Line 41, "Z is nitrogen; and" should read -- Z is nitrogen; --.

Signed and Sealed this

Twelfth Day of April, 2005

JON W. DUDAS
*Director of the United States Patent and Trademark Office*